(12) United States Patent
Morin et al.

(10) Patent No.: US 12,343,057 B2
(45) Date of Patent: Jul. 1, 2025

(54) DISCRETE DERIVATIVE DIFFERENTIAL CIRCUIT DRIVEN SYSTEM AND METHODS FOR DETERMINING THE CURE OF PMMA INTRAOPERATIVELY AFTER IMPLANTATION OF AN ORTHOPEDIC DEVICE

(71) Applicant: WAVETEST, LLC, Cincinnati, OH (US)

(72) Inventors: Craig E. Morin, Galena, OH (US); Gary E. Myers, New Albany, OH (US); Daniel A. Funk, Cincinnati, OH (US); Quang-Viet Nguyen, Aldie, VA (US)

(73) Assignee: WAVETEST, LLC, Cincinnati, OH (US)

( * ) Notice: Subject to any disclaimer, the term of this patent is extended or adjusted under 35 U.S.C. 154(b) by 454 days.

(21) Appl. No.: 17/939,378

(22) Filed: Sep. 7, 2022

(65) Prior Publication Data
US 2023/0210572 A1 Jul. 6, 2023

Related U.S. Application Data

(63) Continuation-in-part of application No. 17/617,441, filed as application No. PCT/US2021/021941 on Mar. 11, 2021.
(Continued)

(51) Int. Cl.
*A61B 17/88* (2006.01)
*A61B 34/30* (2016.01)
(Continued)

(52) U.S. Cl.
CPC .......... *A61B 17/8836* (2013.01); *A61B 34/30* (2016.02); *G01R 19/0038* (2013.01);
(Continued)

(58) Field of Classification Search
CPC ............ A61B 17/8836; A61B 17/8841; A61B 2017/00088; A61B 2017/00128;
(Continued)

(56) References Cited

U.S. PATENT DOCUMENTS 4,455,268 A 6/1984 Hinrichs et al.
4,515,545 A 5/1985 Hinrichs et al.
(Continued)

OTHER PUBLICATIONS

Yao et al., Power ultrasound and its applications: A state-of-the art review, Ultrasonics—Sonochemistry, 2020, pp. 1-20, Elsevier B.V.
(Continued)

*Primary Examiner* — Samuel S Hanna
(74) *Attorney, Agent, or Firm* — Hudak, Shunk & Farine Co. LPA

(57) ABSTRACT

The invention comprises a system for securing an implant to a bone comprising an implant which is affixed to the bone, a grout or bone cement comprising a composition that cures in an exothermic reaction and which is capable of securing the implant to the bone in a cured state, and a tester which measures temperature over time to detect a rate change of temperature and uses a novel discrete differentiator circuit to determine when the composition reaches cure.

10 Claims, 9 Drawing Sheets

Related U.S. Application Data

(60) Provisional application No. 62/989,227, filed on Mar. 13, 2020, provisional application No. 63/111,318, filed on Nov. 9, 2020, provisional application No. 63/343,345, filed on May 18, 2022.

(51) Int. Cl.
*G01R 19/00* (2006.01)
*A61B 17/00* (2006.01)

(52) U.S. Cl.
CPC ............... *A61B 2017/00088* (2013.01); *A61B 2017/00128* (2013.01)

(58) Field of Classification Search
CPC ..... A61B 34/30; A61B 17/8802; A61B 17/88; A61B 17/8805; A61B 17/8808; A61B 17/8811; A61B 2017/8813; A61B 17/8816; A61B 17/8819; A61B 17/8822; A61B 17/8825; A61B 2017/883; A61B 2017/8844; A61B 17/8847; A61B 17/8833; A61B 2017/8838; G01R 19/0038
See application file for complete search history.

(56) References Cited

U.S. PATENT DOCUMENTS

| | | | |
|---|---|---|---|
| 4,559,810 A | 12/1985 | Hinrichs et al. | |
| 4,574,637 A | 3/1986 | Adler et al. | |
| 4,590,803 A | 5/1986 | Harrold | |
| 4,758,803 A | 7/1988 | Thomas, III | |
| 4,874,948 A | 10/1989 | Cielo et al. | |
| 4,891,591 A | 1/1990 | Johnston et al. | |
| 4,904,080 A | 2/1990 | Afromowitz | |
| 5,009,104 A | 4/1991 | Johnson | |
| 5,145,250 A | 9/1992 | Planck et al. | |
| 5,911,159 A | 6/1999 | Choo et al. | |
| 6,644,122 B2 | 11/2003 | Borowczak et al. | |
| 6,675,112 B1 | 1/2004 | Chadwick | |
| 7,245,371 B2 | 7/2007 | Wang et al. | |
| 8,419,640 B1 | 4/2013 | Saha | |
| 9,297,789 B2 | 3/2016 | Djordjevic et al. | |
| 2006/0123914 A1 | 6/2006 | Pena et al. | |
| 2007/0154874 A1 | 7/2007 | Sherman et al. | |
| 2007/0270786 A1 | 11/2007 | Higham et al. | |
| 2009/0084978 A1 | 4/2009 | Chandler et al. | |
| 2009/0112365 A1 | 4/2009 | Orr et al. | |
| 2010/0087827 A1 | 4/2010 | Baroud | |
| 2010/0110436 A1* | 5/2010 | Chandler | A61B 17/8802 702/176 |
| 2013/0035561 A1 | 2/2013 | Sharkey et al. | |
| 2021/0302374 A1 | 9/2021 | Jack | |

OTHER PUBLICATIONS

Price et al., Polymerization of Methyl Methacrylate Initiated by Ultrasound, Macromolecules, 1992, pp. 6447-6454, vol. 25, American Chemical Society.

Arenas-Arrocena et al., New Trades for the Processing of Poly(Methyl Methacrylate) Biomaterial for Dental Prosthodontics, 2017, pp. 43-74, Chapter 3, Intech.

Dunne et al., Ultrasonic characterization of the mechanical properties and polymerization reaction of acrylic-based bone cements, Journal of Engineering in Medicine, 2007, pp. 251-261, vol. 221.

Mchugh, Ultrasound Technique for the Dynamic Mechanical Analysis (DMA) of Polymers, BAM-Dissertationsreline-Band31, 2008, pp. 1-146, Berlin.

Lionetto et al., Monitoring the Cure State of Thermosetting Resins by Ultrasound, Materials (Basel), 2013, pp. 3783-3804, MDPI.

\* cited by examiner

| Temp | Cool | Hot | Cool |
|---|---|---|---|
|  | V1>V2 | V2>V1 | V2>V1(LATCH+) |
| CMP1 | Off | On | Off |
| LATCH | Off | On | On |
| CMP2 | On | Off | On |
| AND1 | Off | Off | On |

FIG. 4

Simplified System Overview

Discrete Time Differentiator

Differentiator

DISCRETE DERIVATIVE DIFFERENTIAL CIRCUIT DRIVEN SYSTEM AND METHODS FOR DETERMINING THE CURE OF PMMA INTRAOPERATIVELY AFTER IMPLANTATION OF AN ORTHOPEDIC DEVICE

FIELD OF THE INVENTION

The field of this invention is in the area of medical devices, and in particular, medical device systems relating to assurance as to the cure of bone cement during surgery, as well as to methods of use of the devices, including surgical methods using the system.

In a further embodiment, the field of this invention is in the area of electronic devices having censers to determine an event, and in particular, medical device systems relating to assurance as to the cure of bone cement during surgery. Further it relates to a novel analog electronic circuit for determining the inflection point or maximum rate of temperature change (i.e., the first derivative of the plot of temperature over time) of the exothermic cure process of bone cement.

BACKGROUND OF THE INVENTION

The present invention addresses issues relating to a method for the determination of the state of cure of bone cement or grout used in present surgical procedures. The state of the art for determining full curing of the PMMA intraoperatively is problematic, as the state of cure is determined either by direct palpation of the PMMA edge or by allowing extra PMMA not used in the surgical implantation to harden.

Acrylic bone cement has been used in orthopedic surgery for over fifty years and is the standard of care for fixation of total joint arthroplasty. After mixing the liquid monomer with the powdered polymer, the cement converts from liquid to solid by an exothermic reaction. The duration of full polymerization is variable and depends on multiple factors, including temperature and humidity. The ASTM Standard specification for full cement curing in a testing environment is based on the temperature of the cement (shown in FIG. 1). The cure temperature ($T_{cure}$, i.e., the temperature where the cement is considered fully cured) is approximately halfway between the maximum temperature of the cement during curing ($T_{max}$) and the ambient beginning temperature of the cement ($T_{ambient}$). The ASTM method can only be applied retrospectively to determine when the cure point occurred after the maximum temperature is reached.

It is desirable to be able to provide an improved device to determine the full PMMA cure and to document that hardening of the PMMA has been achieved during surgery. More accurate determination would provide for decreased surgical time and better protection from PMMA implant bond breakage.

Presently, cement curing during implant surgery is determined either by palpating the cement edge or by allowing the remainder cement to harden in vitro. Both methods are imprecise and unscientific. Intraoperative observation by surgeons has noted that in vivo cement appears to cure faster than the remaining excess cement in vitro. This is likely because the in vivo cement is in a warmer and more humid environment.

The significance of cement curing time has become more important with recent investigations into the cause of aseptic loosening of a total knee tibial implant. It has been proposed that lipid infiltration between the tibial tray and the cement interface prevents the cement from interdigitating with the undersurface of the tibial tray, resulting in an area of de-bonded cement. Motion prior to full cure of the tibial tray cement can hydraulically wick lipids into the cement-tray interface. As a result, accurate determination of curing of the cement under the tibial tray before knee motion during total knee arthroplasty is important.

Aseptic loosening of the tibial plateau base plate after total knee arthroplasty remains one of the primary reasons for revision surgery of total knee arthroplasty. There is evidence that breaking of the cement implant bond at the time of surgery is a contributor to the development of aseptic loosening. Movement of the knee prior to cement cure can be a cause of migration of lipids under the base plate and breaking of the cement implant bond. Recent focus has been on lipid infiltrating under the tibial tray. This infiltration prevents the cement from obtaining a secure mechanical bond on the tibial tray. New tibial implant designs have been developed to decrease the possibility of lipid infiltration. Motion of the knee prior to cement cure can increase the risk of lipid infiltration and subsequent debonding, even with the new tray designs, motion of the knee prior to cement cure remains a possible source of aseptic loosening.

The present invention provides a further embodiment to confirm that a method using temperature sensors to monitor the rate of temperature change can be used to accurately determine tibial tray cement cure and could shorten the operative time of total knee replacement. The novel discrete time differentiation circuit of the present invention is useful in this method and may have additional applications as well.

The present invention provides a novel system for broadly determining a threshold event based upon a derivative of a signal that changes too slowly to effectively use the traditional op-amp differentiator topology, or is potentially subject to noise or the need for high signal amplification. It is particularly useful in applications such as the first embodiment and which involves small, affordable, analog components and which require low cost and low power operation, such as the present use in a temperature rise based cure censer system for use in determining the state of cure of orthopedic surgical cement.

This invention is novel as a system which serves a specific purpose in a monitor for cement cure and further utilizes a novel circuit. This circuit includes a discrete time derivative determiner (or "numerical differentiation") which consists entirely of analog electronics and is useful for slow moving signals, such as the temperature change resulting from the polymerization process of bone cement in use. This circuit is useful in the present invention since the normal continuous approach to analog differentiation does not handle a slow-rising temperature well and an increase in gain presents an increase in the noise.

The invention could include yet a further embodiment using digital or software implementation which would be based upon a similar concept in theory since the thermistor used for temperature determination would be sampled by an analog-to-digital converter into discrete samples and then used for computing the derivative; however, this approach introduces the need for additional design controls to reduce software risk.

At the core of the present invention is a sample and hold circuit combined with a difference amplifier. This circuit advantageously uses a JFET (junction field-effect transistor) component but could similarly use MOSFET components or analog switches instead, although potentially in a larger footprint or complexity or for a higher price. The output of the difference amplifier is fed into a peak hold circuit to capture the peak derivative. New peaks reset a digital timer and the maximum peak event is indicated when the timer is not reset by a new peak before reaching a pre-defined maximum time interval. The invention can be implemented to track first derivative peaks in either direction but the present application only requires detecting peaks due to a temperature rise.

The present invention also addresses issues relating to a device using this circuit and to a method for the determination of the state of cure of bone cement or grout used in present surgical procedures. The current state of the art for determining full curing of the PMMA intraoperatively is problematic, as the state of cure is determined either by direct palpation of the PMMA edge or by allowing extra PMMA not used in the surgical implantation to harden.

SUMMARY OF THE INVENTION

The present invention addresses issues relating to cure of bone cement or grout which is used in conjunction with present surgical procedures. In particular, the present invention provides a system having a temperature sensor that allows the user to monitor a reaction of the substance and to receive an alert when a set condition has occurred.

In a more specific embodiment, the system of the present invention enables a surgeon to make an accurate and reproducible bead of cement which undergoes an exothermic reaction during cure. The system enables the user to place a temperature sensor in the cement in situ during major orthopedic surgery, such as, for example total knee replacement surgery. This system comprises a system including a sensor which is joined to an alarm to alert the user of the state of the cement.

A method of using the system is accomplished within an established work-flow method, and by using a tester including a temperature sensor such as a thermistor, thermocouple, or other electronic device that converts a temperature into a signal that can be processed using either and analog or digital means. Advantageously, in accordance with one aspect of the present embodiment of the invention, a novel analog circuit is provided to determine the maximum peak rate of temperature change of the cement to signal cure.

Typically, temperature changes are registered as voltage changes which can be analyzed using analog circuits to provide outputs to a logic circuit operatively joined to an indicator, such as a display, light, alarm, haptic indicator or robotic surgical device. In particular, this invention monitors the rate of change of the temperature of the exothermic reaction of the cement and couples a clock to a sample and hold circuit with a difference amplifier in a single stage. Alternatively, the derivative of the temperature signals can be digitized using an analog to digital converter (ADC) and the digital representation of the temperature is analyzed to drive a logical indicator.

BRIEF DESCRIPTION OF THE DRAWINGS

FIG. 4 is a logic table for the cement cure;

DETAILED DESCRIPTION OF THE INVENTION

The standard means for stabilizing orthopedic implants used in total joint arthroplasty is grouting with an acrylic (poly methyl methacrylate—PMMA) material. In use, the PMMA is supplied in two parts: a powder monomer and a liquid catalyst. These two components are mixed during surgery and proceed from a liquid to a solid at varying rates depending on multiple factors such as temperature and humidity. The PMMA in its compliable state is applied to the bone ends with the implant then being pushed onto the bone with the PMMA between the bone and implant. After hardening, the implant is considered fixed to the bone and motion is allowed. Motion prior to PMMA hardening can lead to lipid infiltration underneath the implant which breaks the bond between the PMMA and the implant leading to loosening and possible need for revision surgery. It is desirable to be able to provide a better means to determine the full cure and to document that hardening of the PMMA has been achieved during surgery. More accurate determination would provide for decreased surgical time and better protection from PMMA implant bond breakage.

Figure 1:
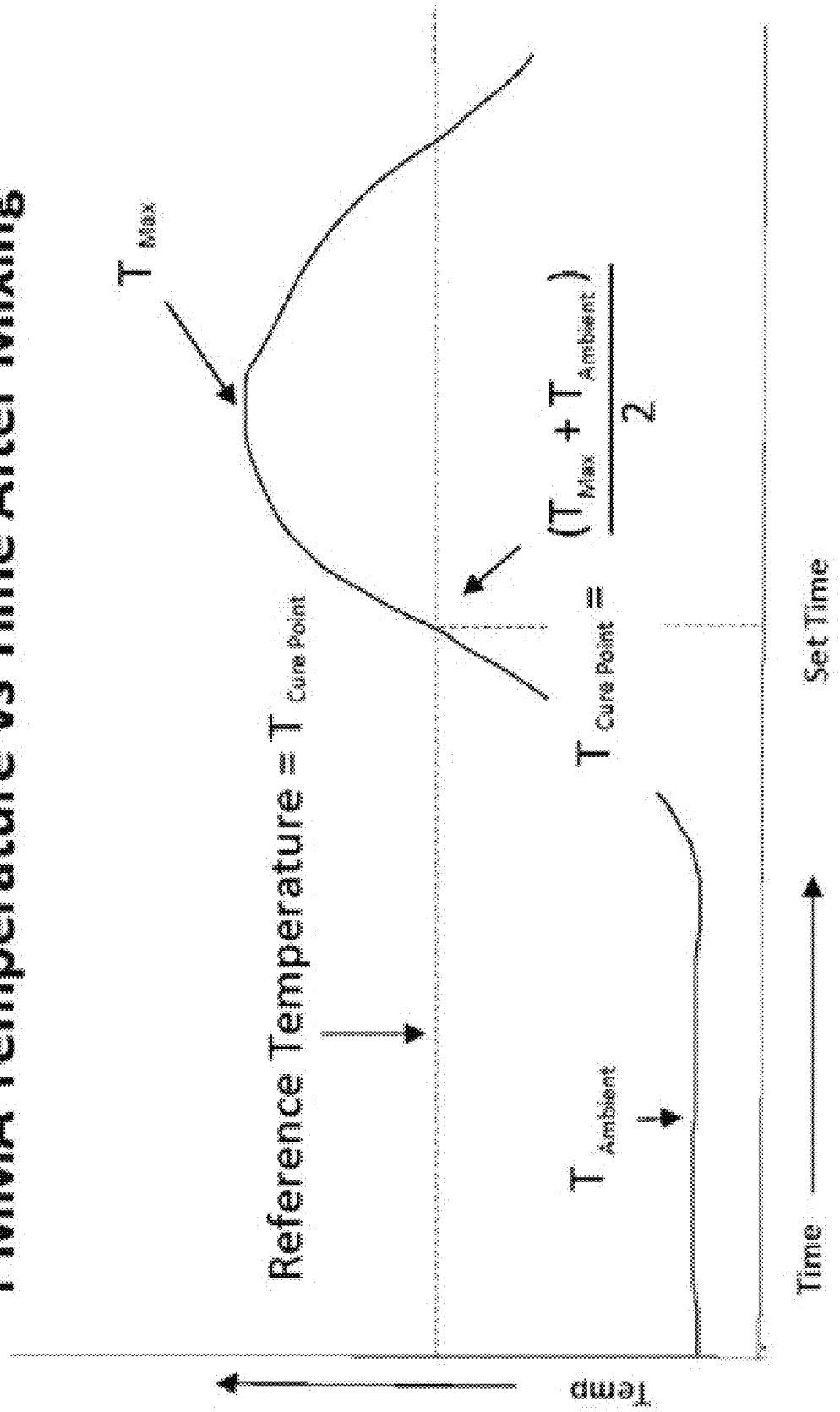
FIG. 1 is a plot of time vs temperature for the cure of PMMA after mixing.

PMMA undergoes an exothermic reaction during cure. During the phase transition of PMMA from liquid to solid (curing) the exothermic reaction has a thermal curve shown in FIG. 1.

PMMA cure temperature is represented by Reference Temperature ($T_{Cure\ Point}$) which is determined in a calculation between the maximum temperature and the ambient temperature. This cure point has been standardized for Orthopedic PMMA as referenced in the ASTM Designation: F451-16, "Standard Specification for Acrylic Bone Cement of the Joint in Preparation of Finishing the Surgery."

Figure 2:
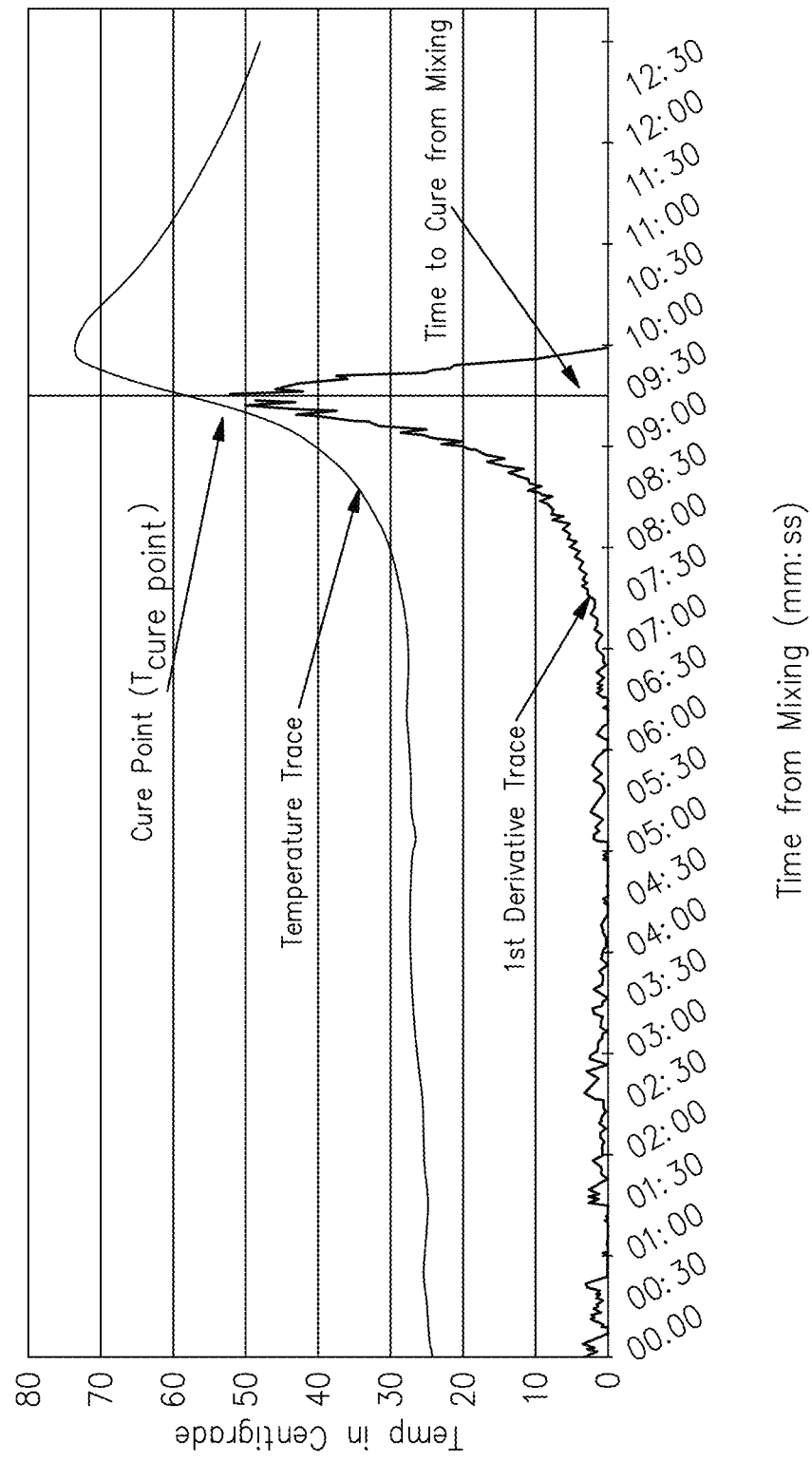
FIG. 2 is a plot of the first derivative values of the temperature changes over time.

The present invention uses this tester to monitor the temperature of the PMMA after placement of the orthopedic implant onto the bone. This is accomplished by insertion of a temperature sensor, such as a thermistor which is a component of the probe into the PMMA in situ. The system of the present invention also includes a guide to provide access to the cement actually used to stabilize the bone construct (i.e., "in situ"). The current flow changes are registered in the thermistor with the temperature of the PMMA and can be calibrated to specific parameters. More particularly, the present invention monitors the rate of change (i.e., the derivative) of the temperature of the cement during cure or polymerization. This is illustrated in FIG. 2 where the cure is shown as a peak at roughly 9.5 minutes from start.

A preferable temperature sensor for use in the present invention is a semiconductor-based negative temperature coefficient (NTC) thermistor which may be mounted on an insertion probe in contact with cement in place or as a sample during the cure process. Positive temperature coefficient (PTC) sensors can also be used along with metal thermocouples, or even P-N junction-based diodes. The NTC thermistor is convenient to use as it has been highly developed to provide a low-cost and accurate sensor (up to 0.02 degrees C. accuracy) in a compact package such as small bead buried inside a flat hermetically-sealed casing.

Figure 3:
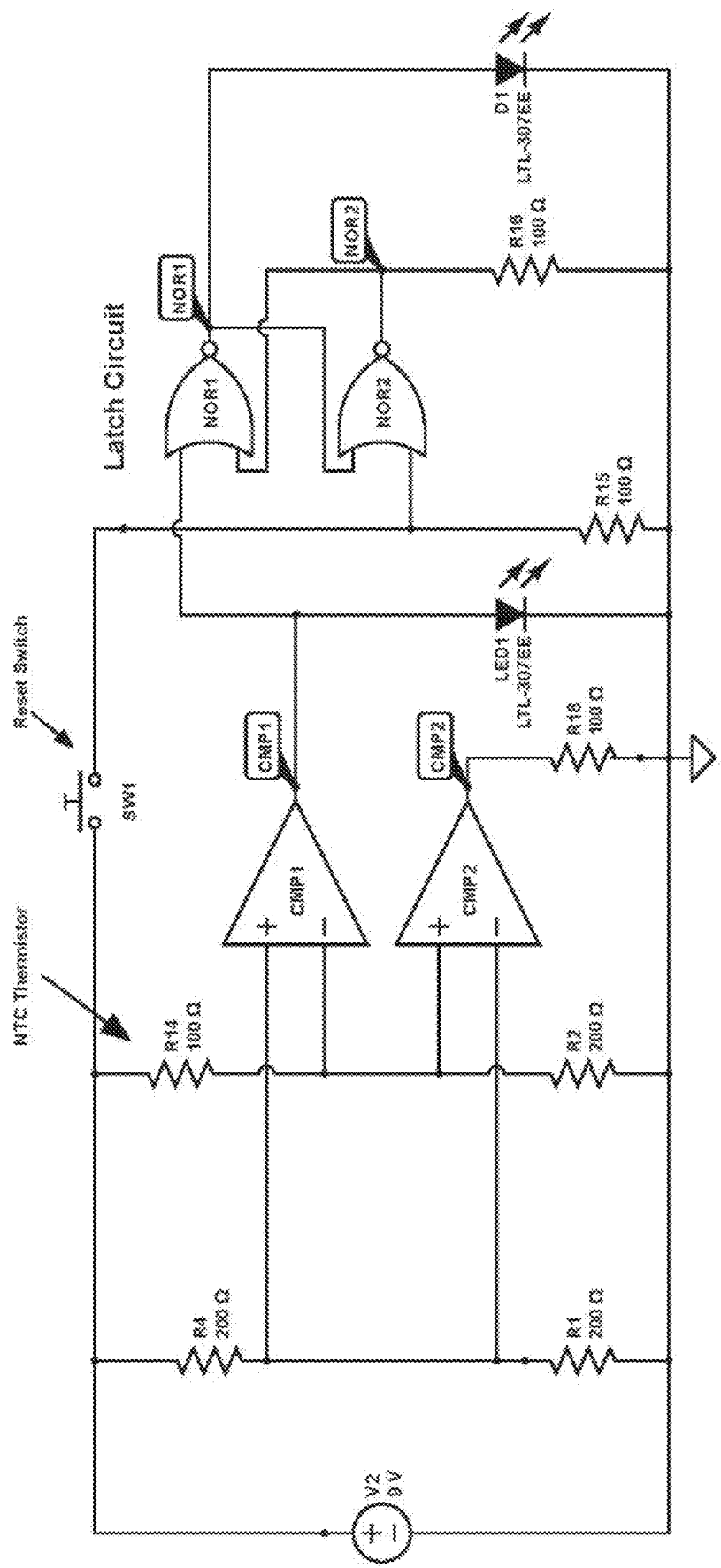
FIG. 3 is a diagram showing a circuit for a cement cure sensor in accordance with the invention.

FIG. 3 shows a schematic diagram of a first version of the invention and which describes a circuit using a NTC variable resistor whose resistance decreases with increasing temperature. The resistor R1 provides the voltage of the reference temperature ($T_{Cure\ point}$). The voltage across R2 is variable in response to the resistance thermistor in series. As the thermistor is heated, the current will increase and the voltage reading for R2 will increase. In a first version of the present tester using solid state comparators CMP1, the two voltages are compared. A lower V1 to V2 ratio indicates that the PMMA temperature is below the Reference Temperature ($T_{Cure\ Point}$) and a higher V1 to V2 ratio indicates PMMA temperature above the Reference Temperature ($T_{Cure\ Point}$).

When the PMMA temperature is low, CMP1 will be on and CMP2 will be off, whereas when the PMMA temperature is high CMP1 will be on and CMP2 will be off.

The output of the comparators is then analyzed through a logic circuit. CMP1 is attached to the set lead of a digital latch. When the Set is initiated by a positive (on) signal, the latch is initiated, and the output of the latch remains positive (on) until the reset is initiated. As a result, once the reference temperature ($T_{Cure\ Point}$) is reached, the output of CMP1 turns positive (on) and remains positive (on) even when the temperature is below Reference Temperature ($T_{Cure\ Point}$) during cooling. The output of the LATCH and CMP2 are then analyzed through an AND Logic Gate. The output of an AND Gate is negative (off) until both leads are on. The final logic output follows the logic of FIG. 4.

Following the PMMA temperature cure curve, as the PMMA progresses past the $T_{Cure\ Point}$ LED1 is turned on which indicates that the PMMA has cured the joint can be safely moved. Continuing with the temperature curve the thermal response will cool since the reaction is complete. The circuit has primed the Latch Circuit after the first pass through of the $T_{Cure\ Point}$. When the PMMA temperature passes through the $T_{cure\ point}$ a second time as the PMMA cools LED2 is turned. This indicates that the PMMA reaction has stopped and cement is fully hardened.

Figure 5:
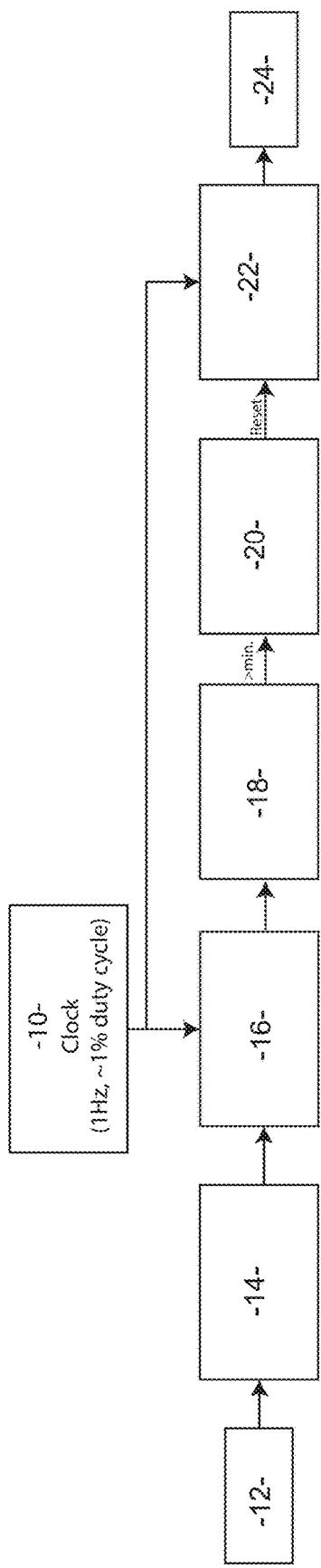
FIG. 5 is a block diagram of the sensor system of the present invention.

FIG. 5 is a block diagram overview of a further version of the present invention which uses the discrete time differentiator circuit 16 described above. The thermistor 12 monitors the temperature of the cement and has a voltage output to a signal conditioning component 14 so as to provide a clean signal to drive the discrete time differentiator 16 which is likewise driven through the input of a 1 Hz clock 10 at approximately 1% duty cycle to sample and hold the input. (These are examples of the clock specifications, but others could be used based on the expected signals.) This allows the system to periodically determine the rate change of the temperature as determined by the NTC thermistor. Power is provided by a clean, regulated power supply, such as a lithium ion battery. The peak outputs of the discrete time differentiator 16, corresponding to the derivative of the current interval, are captured by a peak hold 18 circuit. Once the held peak exceeds a pre-defined minimum threshold monitored with a comparator, the peak hold 18 output is fed to a new peak detector 20 that resets a counter 22 with each new peak. When the counter 22 reaches a maximum count determined by the implementation without a new maximum peak, the cure indicator 24 will alert the user that cure is reached.

Figure 6:
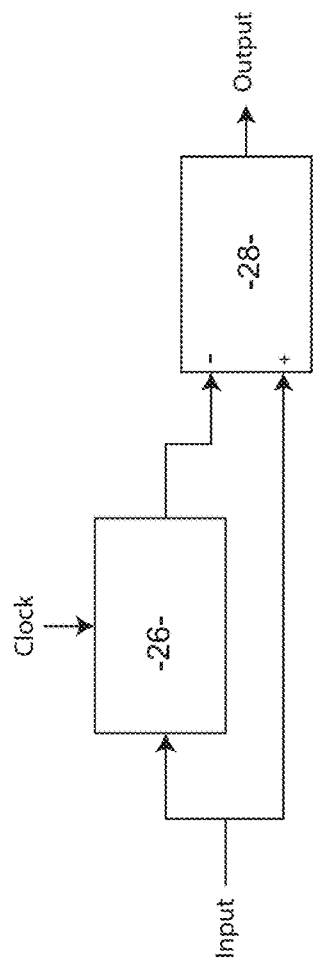
FIG. 6 is a block diagram of the discrete time differentiator of FIG. 4.

FIG. 6 is a block diagram overview for the discrete time differentiator which shows the clock driving the signal hold block 26 which holds the input conditioned signal constant to the negative input of the difference amplifier 28 during the clock hold period. The block diagram further shows the direct input to the positive input of the difference amplifier to allow the stage to amplify the signal change during the hold period (i.e. the slope of the secant from temperature at $time_1$ to temperature at $time_2$) of the exothermic cure as sensed by the cure sensor of the present invention. The output of the difference amplifier 28 is fed to the peak hold 18 block. In the next state of the clock, the signal hold 26 is cleared and both inputs of the difference amplifier 28 are equal and the output returns to zero.

Figure 7:
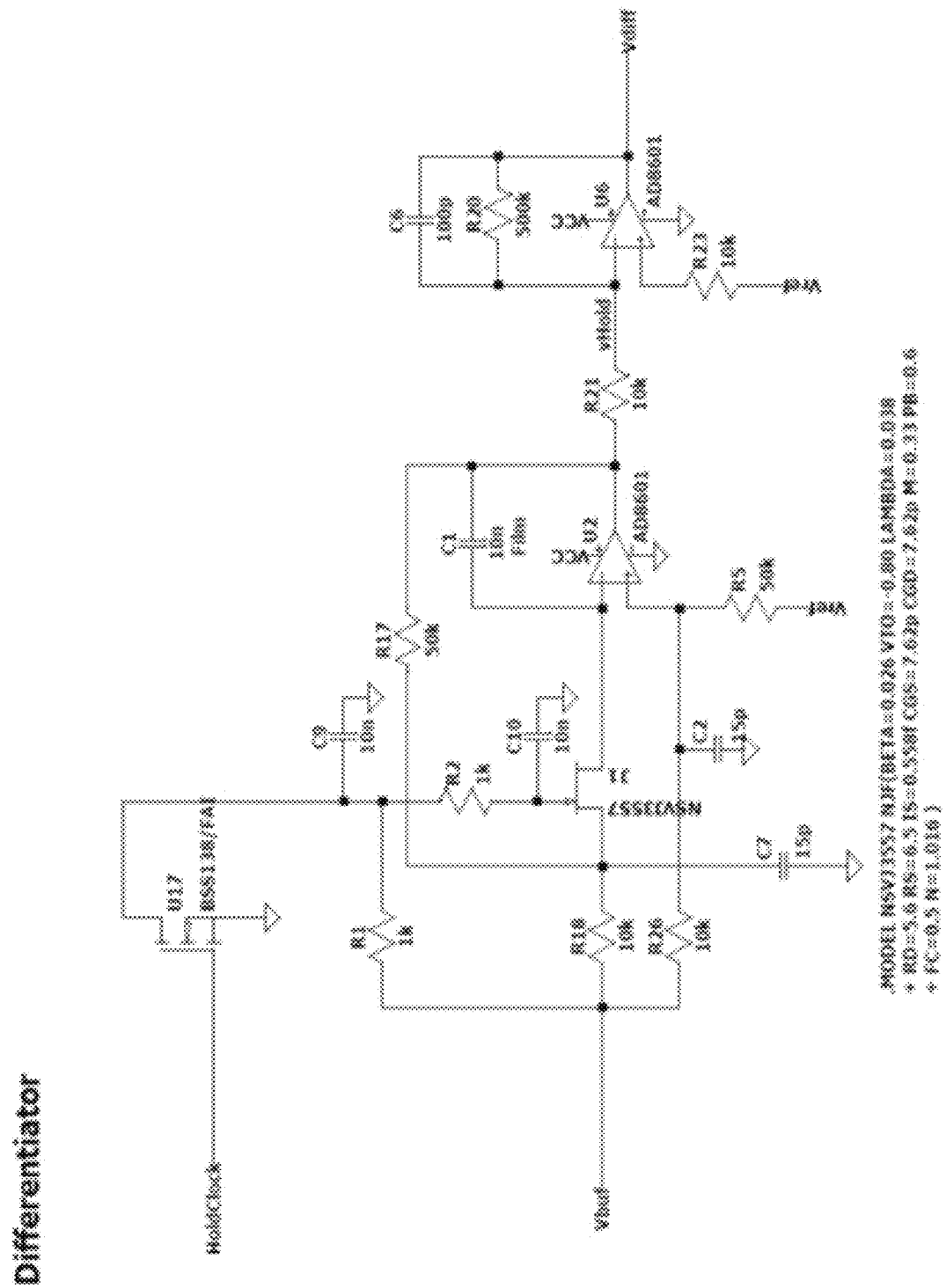
FIG. 7 is a detailed circuit schematic exemplifying the discrete time differentiator of the present invention.

FIG. 7 is a detailed circuit schematic illustrating the single stage differentiator block which includes the clock driving the MOSFET at U17 driving the gate of the JFET at J1 between ground and the input volage Vbuf. While conducting, J1 connects the input voltage to the opamp U2 presenting the same voltage at both the positive and negative terminals of U2 resulting in an output of zero. When J1 ceases conducting, the negative terminal of U2 is only driven by changes to the output voltage of U2 through capacitor C1. Any changes to the input voltage Vbuf while J1 is not conducting results in the change being amplified at the output of U2 multiplied by the ratio of R17/R18, which is equivalent to the ratio of R5/R26. The output of U2 is further amplified and smoothed by the filter around U6 resulting in the output signal Vdiff. This implementation is configured to generate derivative peaks inverted around Vref.

Figure 8:
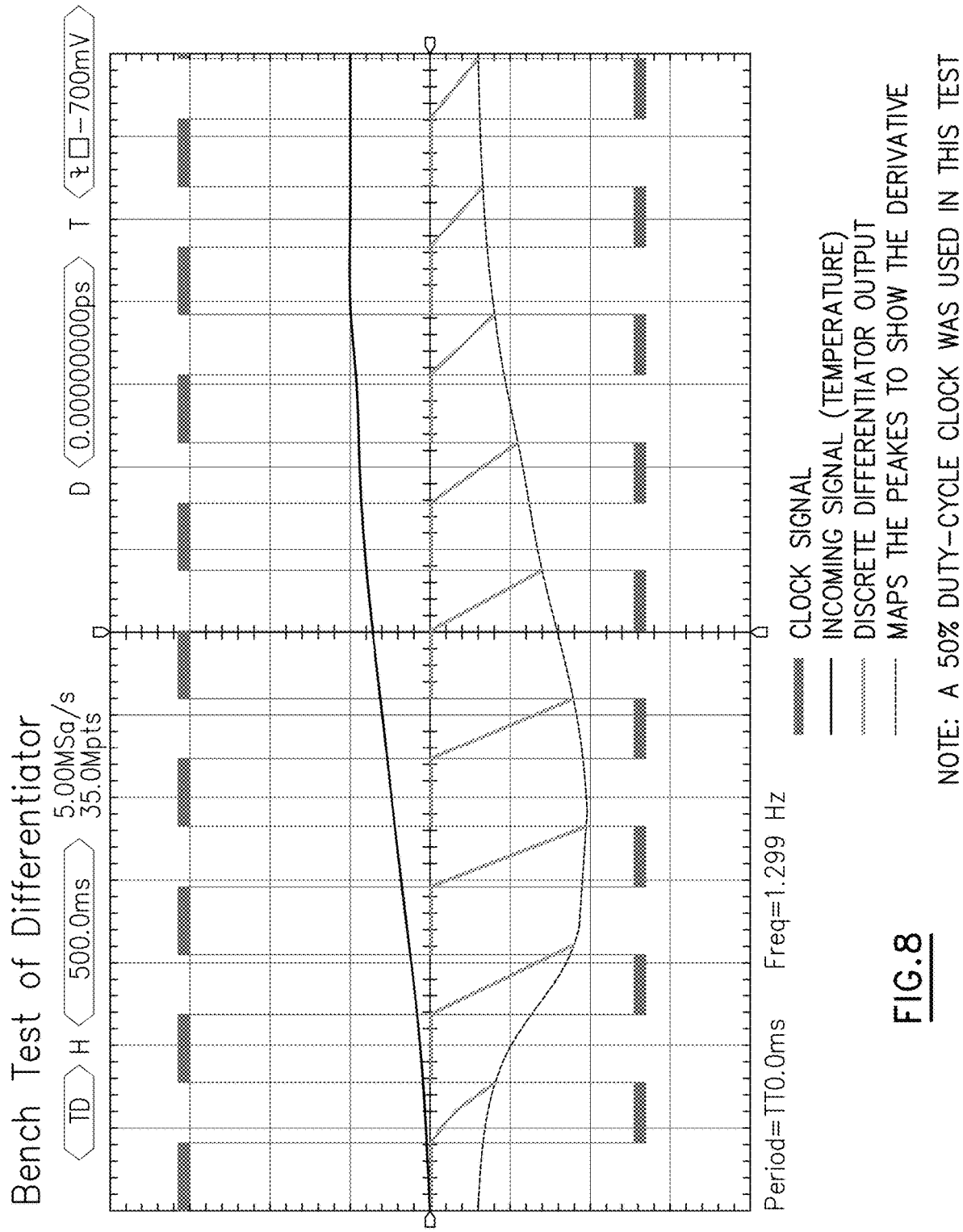
FIG. 8 is a screen shot of a display showing a bench test of the discrete time differentiator of the present invention.

FIG. 8 which illustrates a bench test of the discrete time differentiator where cyan is the clock signal, pink is the incoming temperature signal, yellow is the discrete differentiator output, and red maps the temperature peaks to illustrate the derivative. In this implementation, the derivative is inverted relative to traditional visualizations.

Figure 9:
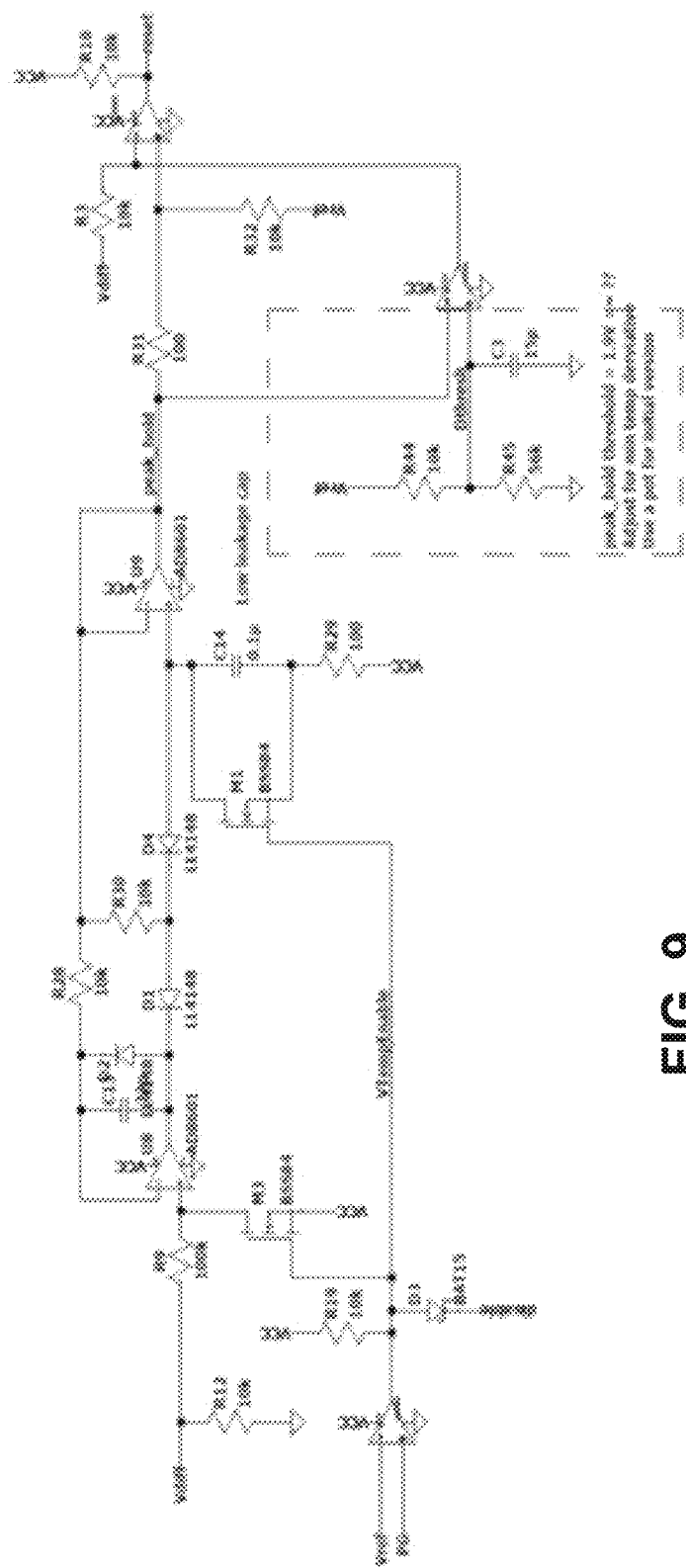
FIG. 9 is a detailed circuit schematic exemplifying the new peak hold, new peak detector and thresholding blocks of the present invention.

FIG. 9 is a detailed schematic of a circuit comprised of a peak hold, threshold gate, and new peak detector. Peak values of the input signal Vdiff are driven by the opamp at U8 to the capacitor at C14. The opamp at U9 feeds back the peak value to sustain the peak value at both terminals of U14 and limit leakage while also passing the maximum peak to the input of the threshold gate at U14. Any input voltages at Vdiff less than the held peak are shunted through D2 and do not affect the maximal peak held by C14 and U9. MOSFETs M3 and M1 clear a held peak during initialization and system reset. The threshold gate at U14 compares the maximal peak found to a minimum threshold set by the voltage created by R44 and R45. Once the maximal peak exceeds the threshold, the new peak detector U5 releases the reset output. While new peaks exceed 99% of the maximal held peak, the new peak detector U5 asserts a reset output which clears a clock in the following stage not illustrated. Other components of the system include the power function, the signal filtering and conditioning function, the counter/clock function, the display or alert component, and the latch or reset function. This implementation is configured to work with inverted derivative peaks where a rising temperature results in a drop in the differentiator voltage. This inversion is specific to this implementation and incidental to the claims. Therefore, it should be understood that the claims apply regardless of whether the derivative is inverted.

Figure 10:
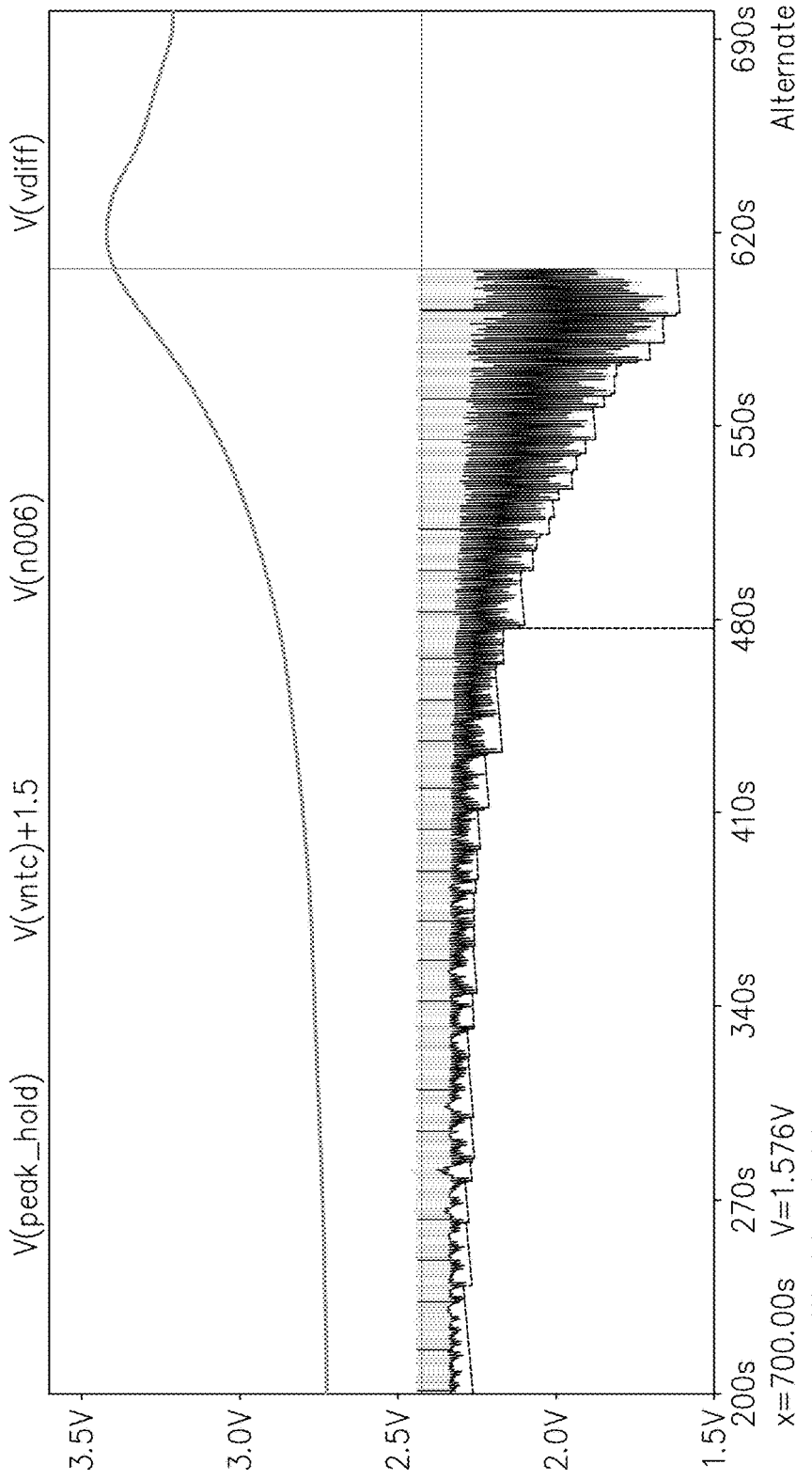
FIG. 10 is a simulation example showing a cure run test using the present invention.

FIG. 10 is a simulation of an example of the use of the present invention showing a discrete derivative plot of the voltage output from the differentiator where red is the temperature signal, green is the differentiator output, cyan is the peak hold, blue indicates when the peak hold (maximum derivative) is above the minimum threshold for measurement and the green peaks stop when no new peak is found within 16 one second cycles (while above the minimum). In this implementation, the derivative is inverted around the midpoint voltage.

Method of Use

The surgical technique using the present cure sensor device will now be detailed. The surgical procedure is initiated, and the bone is made ready to accept the implant. The cement components are mixed to initiate the polymerization or cure process.

The sensor is contacted with the curing cement, either in the mixing vessel or in place on the implant or in the bone. The surgeon then continues with the remainder of the cementing technique in a standard fashion ensuring that cement is placed into the cement hole. The implant is position and impacted and the temperature circuit monitored. After cure of the cement as documented by the inflection point of the temperature of the cement reaching the cure temperature, the sensor is removed from the cement. The remainder of the surgery is performed as per standard protocol. Postoperative care is dictated by surgeon orders.

The following description discusses a determination of the cure point using the present sensor as aided by a programmable microcontroller unit (MCU). Starting with the sensor probe tip in contact with freshly mixed PMMA cement that is still soft and has not yet started to release any heat via its exothermic reaction at step which usually takes about 5 minutes for the mixture to begin reacting and giving off heat which causes the cement mantle to rise in temperature. This period is typically used by the surgeon to apply the cement and to remove excess cement before the hardening process begins. The surgeon or operator then depresses a reset switch to clear any temporary data from the processing unit's memory, and the initial temperature of the uncured PMMA is recorded and assigned as the ambient temperature at $t=t_0$, and the "ARMED" logical value is set as "TRUE" and the associated LED indicator is illuminated. The programmed microcontroller code at this point is in a mode of continuously measuring the temperature of the cement mantle and comparing it against 3 tests using nested IF statements in a loop. The three IF statements check to see if the measured temperature minus the initial ambient temperature (delta Temp) is greater than some nominal value $K_A$ (typically 3C) and if the first derivative of the temperature with respect to time is zero which is indicative of an inflection point, and if the second derivative of the temperature with respect to time is positive relative a nominal value $K_C$ (usually a value circa 0.1 deg $C.^2/sec^2$). The derivatives are calculated using a discrete method with a sliding window of 3 cells. When all three IF conditions are met, then the logical "CURE" variable is set to "TRUE", and the "CURED" LED is illuminated and stays illuminated until the reset switch is depressed, and at this point, the program comes to an end. This program, and its implementation in software for an MCU can also be implemented using analog processors with comparators and op-amps to achieve analog differentiation.

Although the present invention has been described based upon the above embodiments and the data produced by measurement of the performance of the resulting invention that has been reduced to practice, it is apparent to those skilled in the art that certain modifications, variations, and alternative constructions would be apparent, while remaining within the spirit and scope of the invention. In order to determine the metes and bounds of the invention, reference should be made to the following claims.

What is claimed is:

1. A system for securing an implant to a bone, comprising:
    an implant,
    a grout or bone cement in contact with the implant, said grout or bone cement comprising a composition that cures in an exothermic reaction at a temperature x, the grout or the bone cement being capable of securing the implant to the bone in a cured state, and
    a sensor in contact with the grout or bone cement, said sensor continuously monitors derivative of a rate change of the temperature over time of the grout or the bone cement as compared to the ambient temperature to detect the exothermic reaction, and
    the sensor is joined to a cure determinate circuit which includes a discrete derivative differentiator to determine when the rate change of the temperature reaches an inflection point;
    and joined to an indicator that emits a signal in response to a current emitted to the circuit by the sensor to alert the user that the cure is reached.

2. The system for securing an implant to a bone as set forth in claim 1, wherein the signal is an audio signal, visual signal or haptic signal or signal to a robotic device.

3. The system for securing an implant to a bone as set forth in claim 1, wherein the cure determinate circuit comprises analog components.

4. The system for securing an implant to a bone as set forth in claim 1, wherein the cure determinate circuit is a sample and hold circuit with a difference amplifier.

5. The system for securing an implant to a bone as set forth in claim 4, wherein the difference amplifier feeds into a peak hold circuit to periodically capture peak values and to determine a maximum peak value above a pre-defined minimum threshold at a maximum rate of temperature change.

6. The system for securing an implant to a bone as set forth in claim 5, wherein peak hold circuit compares peak values to determine the maximum peak value, and wherein when it determines a new maximum peak value it resets a timer, and a maximum peak value event is indicated when the timer is not reset by a new maximum peak value before reaching a pre-defined maximum time interval.

7. The system for securing an implant to a bone as set forth in claim 6, wherein the peak values comprise the differential voltage which is output from a thermistor which is driven by an operational amplifier to a capacitor and the operational amplifier feeds a peak value back to the circuit to limit voltage leakage and to enable the maximum peak value to be passed to the input of a threshold gate.

8. The system for securing an implant to a bone as set forth in claim 7, wherein an input voltage at the capacitor which is below the input voltage of a previously determined maximum peak value is shunted away so that it does not affect the input voltage of the previously determined maximal peak value.

9. The system for securing an implant to a bone as set forth in claim 8, wherein the determinate circuit comprises MOSFETs or analog switches.

10. The system for securing an implant to a bone as set forth in 9, wherein when a new peak value exceeds a pre-determined fraction of a maximum held peak, value a new peak value detector asserts a reset output to clear a clock or counter.

* * * * *